United States Patent [19]
Klein et al.

[11] Patent Number: 6,083,222
[45] Date of Patent: Jul. 4, 2000

[54] DEFLECTABLE CATHETER FOR ABLATING CARDIAC TISSUE

[75] Inventors: George J. Klein, London, Canada; Josef V. Koblish, Framingham; Thomas T. Coen, Westboro, both of Mass.

[73] Assignee: Boston Scientific Corporation, Natick, Mass.

[21] Appl. No.: 08/730,896

[22] Filed: Oct. 18, 1996

Related U.S. Application Data

[63] Continuation of application No. 08/395,454, Feb. 28, 1995, abandoned.

[51] Int. Cl.[7] .......................... A61B 17/39; A61B 5/0402
[52] U.S. Cl. ................................ 606/41; 606/49; 606/52; 128/642
[58] Field of Search ................................ 606/41, 49, 51, 606/52; 607/99, 122, 126; 128/642

[56] References Cited

U.S. PATENT DOCUMENTS

| | | |
|---|---|---|
| 3,342,175 | 9/1967 | Bulloch . |
| 3,964,468 | 6/1976 | Schulz . |
| 4,184,486 | 1/1980 | Papa . |
| 4,649,924 | 3/1987 | Taccardi . |
| 4,953,559 | 9/1990 | Salerno . |
| 4,960,134 | 10/1990 | Webster, Jr. . |
| 5,083,565 | 1/1992 | Parins . |
| 5,122,137 | 6/1992 | Lennox . |
| 5,133,727 | 7/1992 | Bales et al. . |
| 5,217,458 | 6/1993 | Parins . |
| 5,228,451 | 7/1993 | Bales et al. . |
| 5,281,218 | 1/1994 | Imran . |
| 5,287,857 | 2/1994 | Mann . |
| 5,354,297 | 10/1994 | Avitall ...................................... 607/122 |
| 5,383,874 | 1/1995 | Jackson et al. ........................... 606/41 |
| 5,386,818 | 2/1995 | Schneebaum et al. . |
| 5,482,054 | 1/1996 | Slater et al. . |

FOREIGN PATENT DOCUMENTS

| | | |
|---|---|---|
| 0 317 526 A1 | 5/1989 | European Pat. Off. . |
| 94/07446 | 4/1994 | WIPO . |
| 94/22384 | 10/1994 | WIPO . |

*Primary Examiner*—Lee S. Cohen
*Attorney, Agent, or Firm*—Lyon & Lyon LLP

[57] ABSTRACT

A deflectable catheter for ablating tissue in the heart of a patient comprising: an axially elongated catheter shaft sized and constructed to be advanced through the vasculature of a patient into the patient's heart; a deflection wire; and an ablation electrode having first and second opposed electrically conductive surfaces exposable for contact with a selected area of tissue within the patient's heart and movable with respect to each other to apply gripping force to the contacted area of heart tissue for stabilizing the position of the electrically conductive surfaces of the ablation electrode relative to the selected area of heart tissue. The ablation electrode has a first rigid surface exposed for contact with the vasculature of the patient during advancement of the catheter therethrough and has an electrically conductive second rigid surface exposable for contact with a selected area of tissue within the patient's heart, wherein the axially transverse area circumscribed by the first surface of the ablation electrode is less than the tissue-contacting area exposable by the second rigid surface. Therapeutic treatments of the heart of a patient are also disclosed.

17 Claims, 6 Drawing Sheets

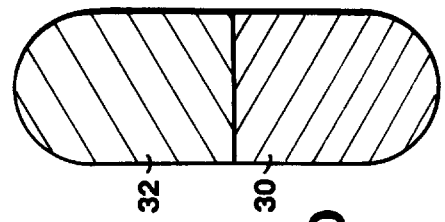
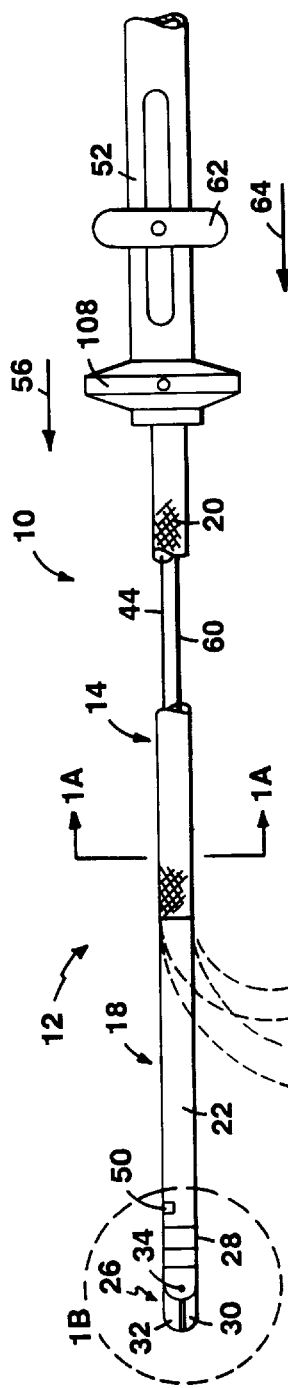
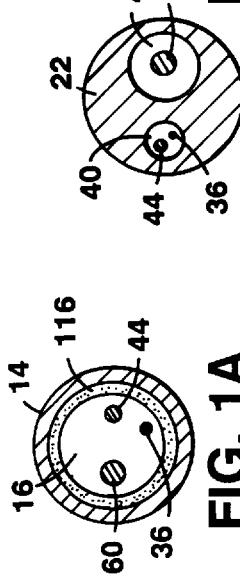
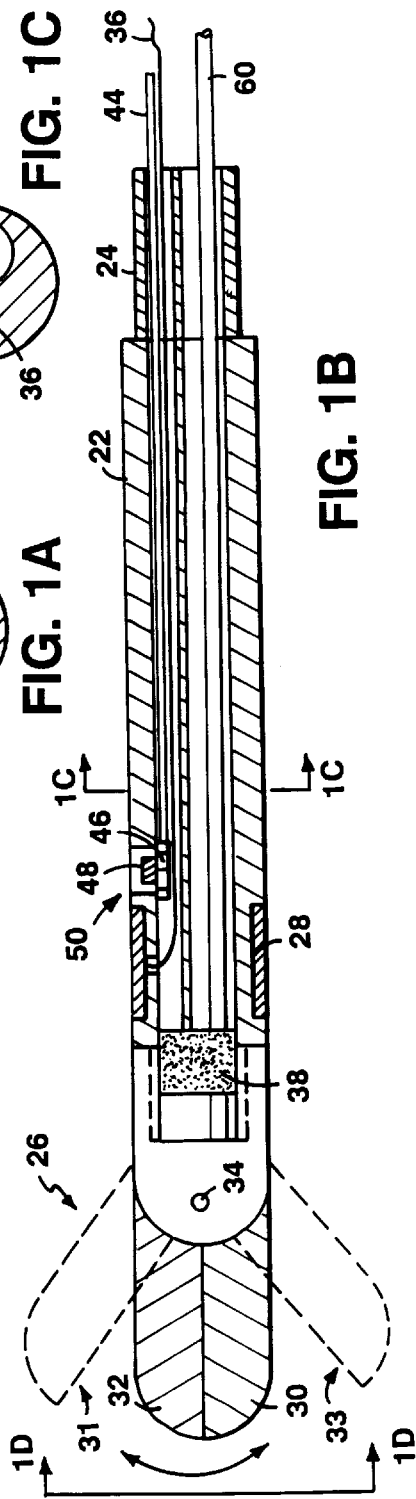

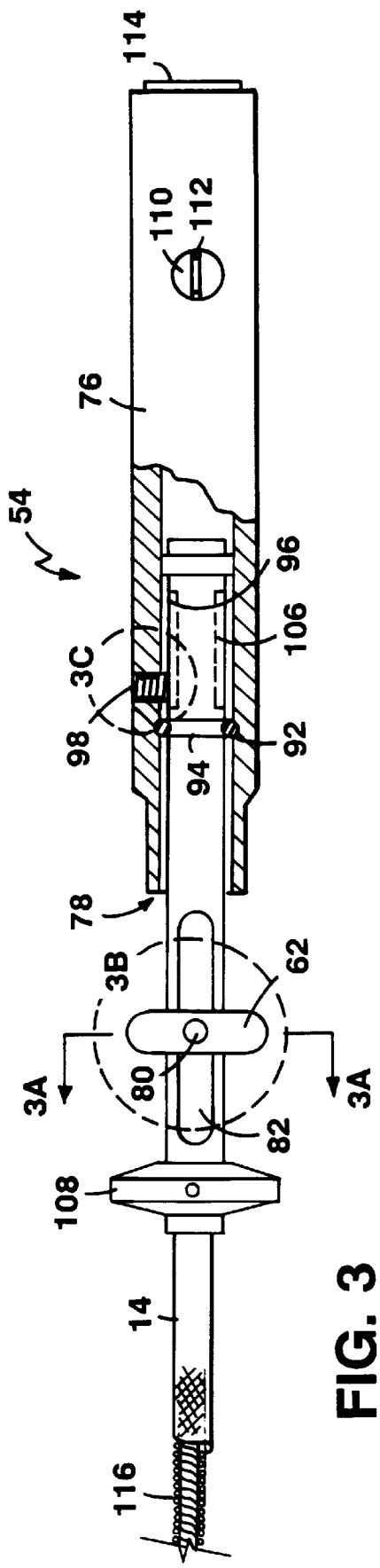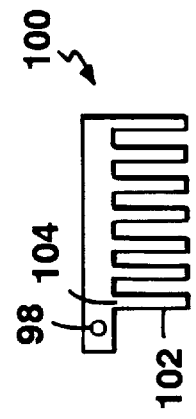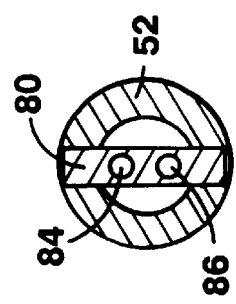

# DEFLECTABLE CATHETER FOR ABLATING CARDIAC TISSUE

This is a continuation of application Ser. No. 08/395,454, filed Feb. 28, 1995, now abandoned.

BACKGROUND

This invention relates to a deflectable catheter for ablating cardiac tissue.

To facilitate the advancement of catheters through a body lumen (e.g., an artery) deflectable catheters have been developed. The simultaneous application of torque at the proximal end of the catheter and the ability to selectively deflect the distal tip of the catheter in a desired direction enables an operator to adjust the direction of advancement of the distal end of the catheter, as well as to position the distal portion of the catheter during, e.g., an electrophysiology procedure.

The distal tip of a deflectable catheter is typically deflected by manipulation of a deflection wire that is attached to the distal end of the catheter and extends to a control handle that controls the application of tension on the deflection wire. In electrophysiology catheter designs it is important to have sufficient flexibility in the catheter shaft so that when the catheter is advanced through a blood vessel the catheter may follow the inherent curvature of the vessel without puncturing the vessel wall. In order to maneuver around turns and bends in the vasculature, an operator observes the catheter fluoroscopically and selectively deflects the tip and rotates the proximal end of the catheter shaft. The ability to control the precise position of the distal end of the catheter depends on the fidelity of the catheter's transmission of the forces exerted at the proximal end to the distal tip. Without high fidelity torque transmission, the operator is unable to control the catheter tip and at best only delays an operating procedure, and at worst may cause the distal tip of the catheter to cause trauma to a patient.

Electrophysiological catheters apply radio frequency energy to produce burn lesions in selected areas of the heart to correct arrhythmias. By destroying the cells that constitute defective conductive pathways, the arrhythmias are stopped.

SUMMARY

In a first aspect, the invention features a deflectable catheter for ablating tissue in the heart of a patient comprising: an axially elongated catheter shaft having proximal and distal portions respectively terminating at proximal and distal ends, the catheter shaft being sized and constructed to be advanced through the vasculature of a patient into the patient's heart; a deflection wire coupled to the distal portion of the catheter shaft and extending within the catheter to the proximal end thereof; and an ablation electrode coupled to the distal end of the catheter shaft and having first and second opposed electrically conductive surfaces exposable for contact with a selected area of tissue within the patient's heart and movable with respect to each other to apply gripping force to the contacted area of heart tissue for stabilizing the position of the electrically conductive surfaces of the ablation electrode relative to the selected area of heart tissue.

In another general aspect, the invention features a deflectable cardiac ablation catheter that includes an ablation electrode coupled to the distal end of the catheter shaft that has a first rigid surface exposed for contact with the vasculature of the patient during advancement of the catheter therethrough and that has an electrically conductive second rigid surface exposable for contact with a selected area of tissue within the patient's heart, wherein the axially transverse area circumscribed by the first surface of the ablation electrode is less than the tissue-contacting area exposable by the second rigid surface.

Embodiments of the invention may include one or more of the following features. An axially elongated actuating member is preferably coupled to the ablation electrode and preferably extends proximally therefrom to the proximal end of the catheter shaft. The actuating member is preferably constructed and arranged to enable selective exposure of conductive surface of the ablation electrode to the selected area of heart tissue. An actuation wire is preferably coupled to the two gripping members and preferably extend proximally therefrom to the proximal end of the catheter for moving the gripping members. A tracking member is preferably coupled to the deflection wire; the tracking member is constructed and arranged to track movement of the actuation wire and to couple tension on the actuation wire to the deflection wire to counteract force applied by the actuation wire to the distal portion of the catheter during movement of the gripping members. The opposed gripping members preferably together form a generally dome-shaped outer surface. The gripping members are preferably solid. The gripping members are preferably pivotally hinged together about a pivot bearing. In certain preferred embodiments, the conductive surface of the ablation electrode that is exposable for contact with the selected area of heart tissue is characterized by mechanical rigidity and flatness over an extended area having transverse dimension of comparable size. In some preferred embodiments, the conductive surface of the ablation electrode exposable for contact with the selected area of heart tissue comprises a plurality of teeth for engaging heart tissue. In some other preferred embodiments, a needle, which is constructed and arranged to penetrate heart tissue to a selected depth, is coupled to the distal end of the catheter shaft.

In another aspect, the invention features a method for the therapeutic treatment of the heart of a patient by ablation of a selected area of heart tissue comprising the steps of: positioning an axially elongated catheter within the heart of a patient, the catheter having a distal ablation electrode with an exposable electrically conductive surface; exposing the electrically conductive surface of the ablation electrode to a selected area of heart tissue; gripping the selected area of heart tissue with the exposed electrically conductive surface of the ablation electrode to stabilize the position of the electrically conductive surfaces relative to the selected area of heart tissue; and ablating the selected area of heart tissue by supplying to the electrically conductive surface of the ablation electrode energy sufficient to achieve tissue ablation.

In yet another aspect, the invention features a method for the therapeutic treatment of the heart of a patient by ablation of a selected area of heart tissue comprising the steps of: providing an axially elongated catheter having a distal ablation electrode adjustable from a closed, low-profile position characterized by a first rigid surface of a selected transverse profile and further having an open position with an electrically conductive second rigid surface exposable for contact with heart tissue over an area larger than the transverse profile characteristic of the ablation electrode in the closed position; advancing the catheter through the vasculature of a patient and into the patient's heart with the ablation electrode in the closed position; adjusting the ablation electrode into the open position to expose the electrically conductive second rigid surface of the ablation electrode for contact with a selected area of heart tissue; contacting the selected area of heart tissue with the electrically conductive rigid surface of the ablation electrode; and ablating the selected area of heart tissue by supplying to the electrically conductive surface of the ablation electrode energy sufficient to achieve tissue ablation.

Embodiments may include one or more of the following advantages.

In certain situations, a distal portion of the catheter is deflected during the therapeutic procedures to increase pressure applied by the exposed conductive surface of the ablation electrode against the selected area of heart tissue. Preferably, the area of heart tissue to be ablated is selected by measuring the electrical potentials within the patient's heart using the catheter positioned within the heart.

The gripping members serve to fix the position of the ablation surface against the area of heart tissue selected to be ablated. This is especially important because the beating of the heart makes it otherwise difficult to maintain the position of the catheter. The gripping members further enhance the ablation of tissue by maintaining a substantially constant pressure against the heart tissue to increase the uniformity and predictability of ablation. The pressure of the ablation surfaces of the gripping members (or any pin or teeth) onto heart tissue effectively clamps the ablation electrode onto the tissue. If the pressure exerted by the ablation electrode against the tissue to be ablated is not constant and if a layer of blood passes between the electrode and the heart wall, there is a chance that the tissue will not be properly ablated and that the blood around the electrode could coagulate. A rigid electrode increases the ability to push against the heart tissue with pressure to cause the heart tissue to conform to the electrode shape and establish good, uniform electrical contact.

The gripping members also have a low profile for delivery into the heart and provide a large area exposable for contact with heart tissue for ablation. A large contact area between tissue and electrode increases the size of the ablated region of tissue and improves the quality of the ablation result. Thus, with a low profile device (e.g., 4 mm transverse diameter), a large area of tissue can be ablated (e.g., 8 mm in length by 4 mm in width). A larger area for ablation also reduces the overall time for the therapeutic procedure, which reduces the patient's discomfort and reduces the risk of the procedure. Thus, the catheter is capable of large area ablations and is sized to access a patient's arterial system, while maintaining maneuverability of the catheter through tight curves in proceeding through the arterial system and into the heart.

The ability to deflect the catheter enables an operator to precisely position the ablation electrode with the patient's heart. In addition, by deflecting the distal tip of the catheter the pressure of the ablation electrode against the heart tissue is increased, further improving the uniformity and effectiveness of tissue ablation.

The catheter achieves high torque transmission without sacrificing flexibility of the catheter shaft, so that the catheter may easily follow the inherent tortuosity of a patient's vasculature without risk of puncture to the patient's vessels. This permits an operator to precisely control the position of the catheter tip during advancement of the catheter through a body lumen, during electro-physiological mapping or ablation of heart tissue.

Other features and advantages of the invention will become apparent from the following.

DESCRIPTION

FIG. 1 is a diagrammatic side view of a deflectable catheter for ablating cardiac tissue.

FIG. 1A is a cross sectional view of the body of the catheter shown in FIG. 1 taken along the line 1A–1A.

FIG. 1B is an enlarged side view, in partial cross section, of the distal tip of the catheter of FIG. 1.

FIG. 1C is a cross sectional view of the catheter tip shown in FIG. 1B taken along the line 1C–1C.

FIG. 1D is a diagrammatic end view of the distal end of the catheter shown in FIG. 1B.

FIG. 3 is a diagrammatic side view, in partial cross section, of the proximal end portion of the catheter of FIG. 1.

FIG. 3A is a cross sectional view of the proximal end of the catheter shown in FIG. 3 taken along the line 3A–3A.

FIG. 3C is a diagrammatic top view of a lock mechanism in the proximal end of the catheter shown in FIG. 3.

Figure 4:
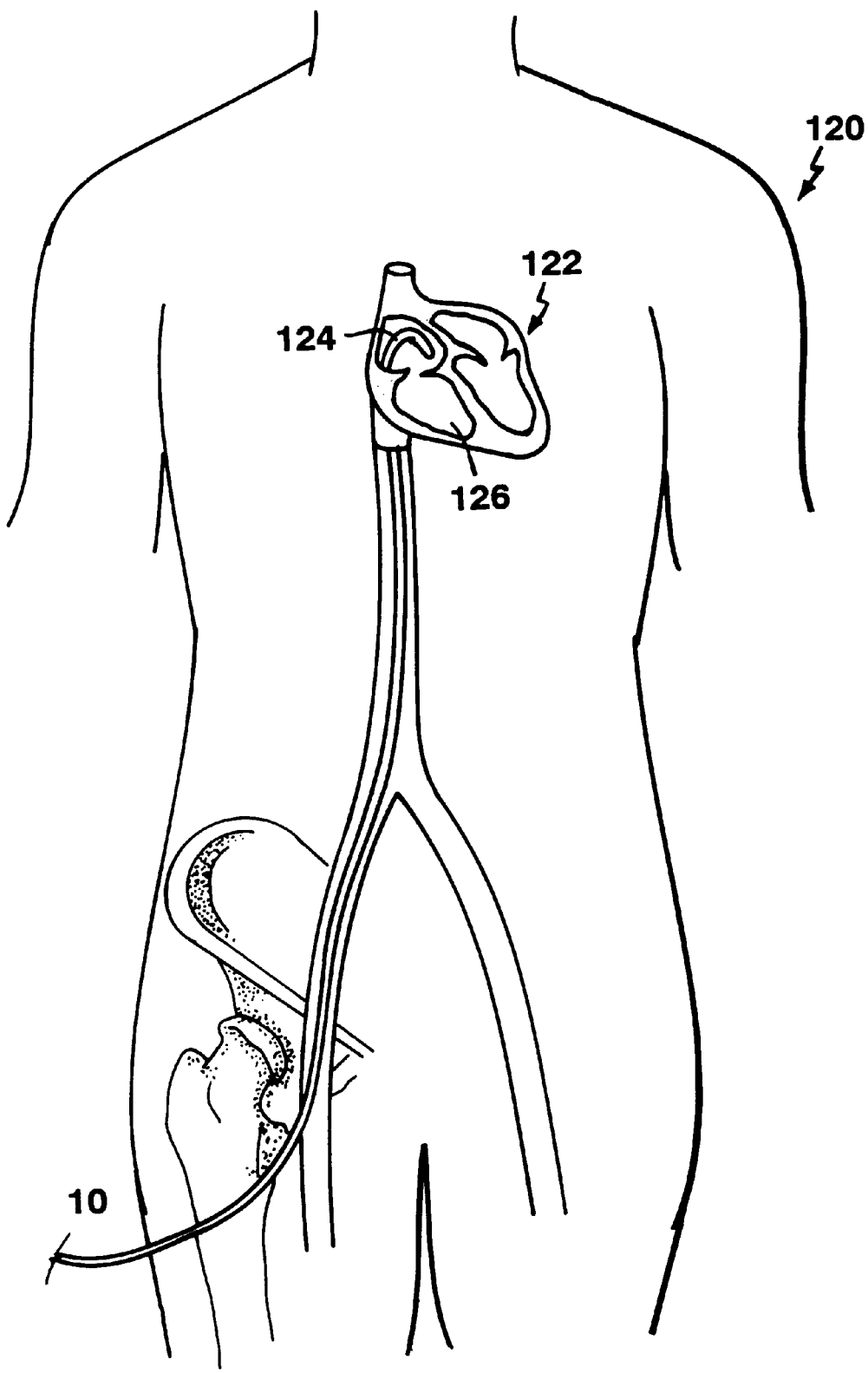
FIG. 4 is a diagrammatic view of the catheter of FIG. 1 disposed within the vasculature of a patient.
Figure 4A:
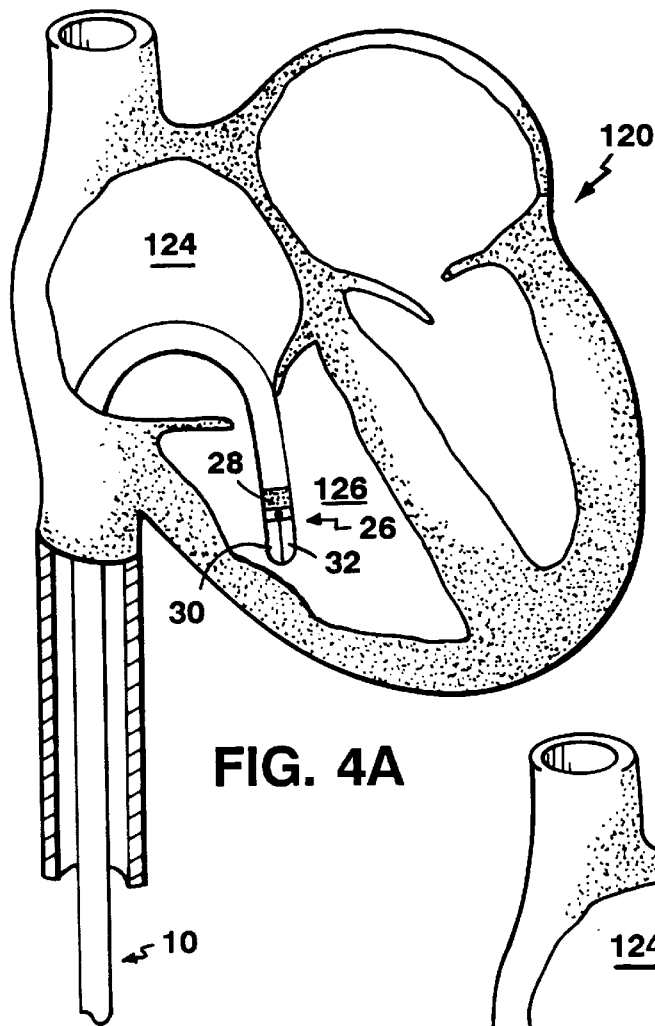
FIG. 4A is a diagrammatic side view of the distal end of the catheter of FIG. 1 positioned within the heart of a patient.
Figure 4B:
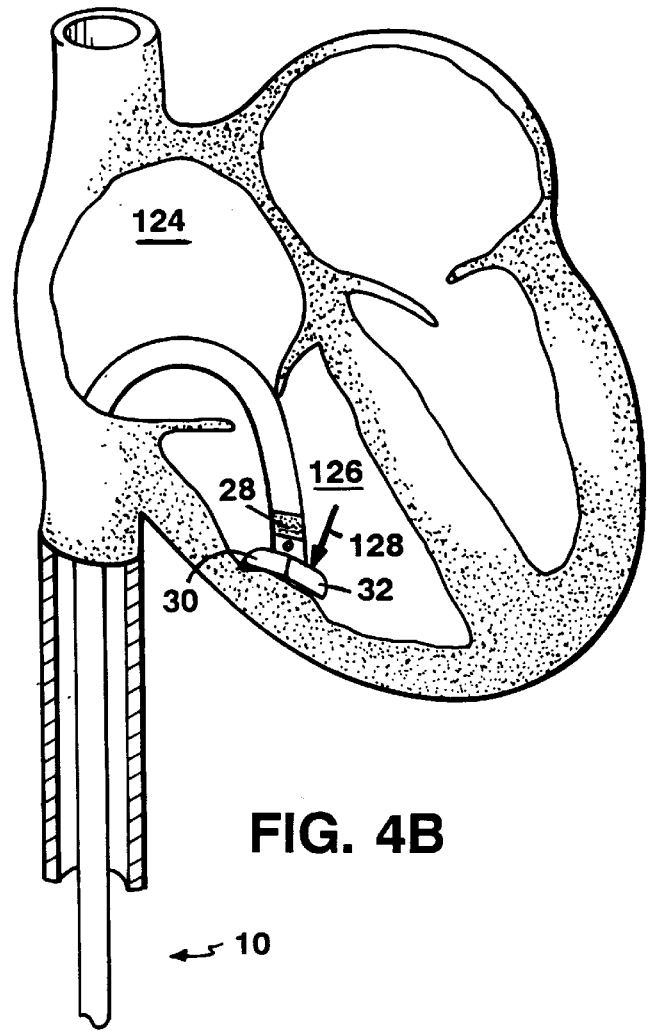

FIG. 4B diagrammatic side view of the distal end of the catheter of FIG. 1 positioned to ablate myocardial tissue within the heart of a patient.

Figure 5:
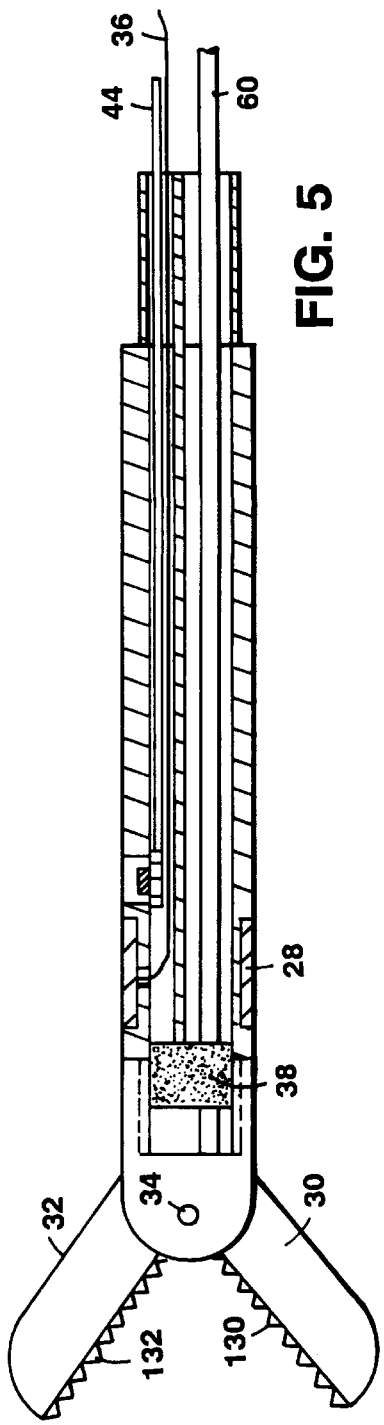

FIG. 5 is a diagrammatic side view, in partial cross section, of the distal end of an alternative deflectable catheter for ablating cardiac tissue.

Figure 6A:
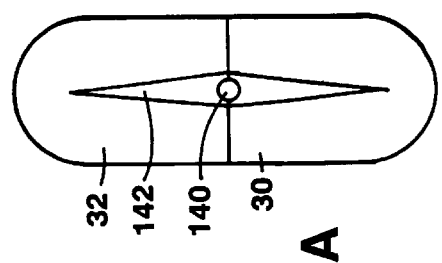
Figure 6:
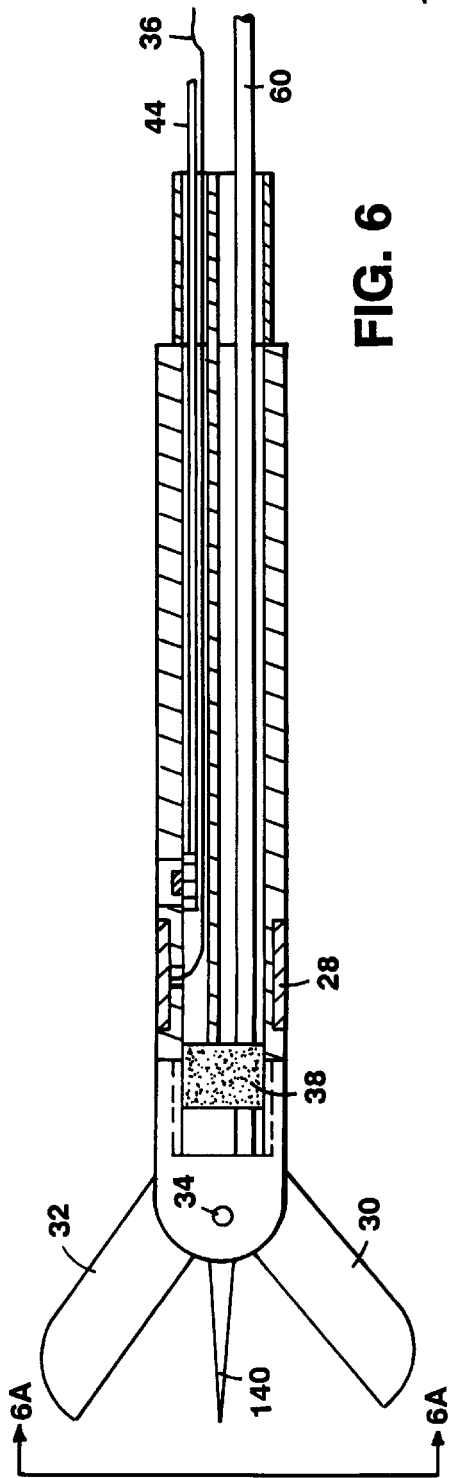

FIG. 6 is a diagrammatic side view, in partial cross section, of the distal end of an alternative deflectable catheter for ablating cardiac tissue.

FIG. 6A is a diagrammatic end view of the distal end of the catheter of FIG. 6.

STRUCTURE

Referring generally to FIGS. 1–1D, a deflectable catheter 10 for ablating cardiac tissue includes an elongated catheter shaft 12 that has a relatively stiff hollow catheter body 14 that defines a lumen 16 and is bonded to a relatively flexible, deflectable distal tip 18. The catheter body includes a braided shaft 20. The distal tip of the catheter is formed from a short section of flexible tubing 22 that is preferably more flexible than the catheter body. The proximal end of the distal tip of the catheter includes a circumferential notch 24 (FIG. 1B) that has an outer diameter selected to snugly fit within the distal lumen of catheter body 14. The catheter tip is bonded to the catheter body using a conventional adhesive.

As shown in greater detail in FIG. 1B, catheter 10 further has an ablation electrode 26 and a ring electrode 28 that are mounted on catheter tip 18. One or more additional ring electrodes may be mounted on the catheter tip, depending on the desired application. Ablation electrode 26 is formed from two opposed gripping members 30, 32 that are pivotally hinged together and movable with respect to each other, about a pivot bearing 34, into a closed position (shown by solid lines) and into an open position (shown by dashed lines). The gripping members are formed of solid electrically conductive material and have respective opposed, flat electrically conductive surfaces that are exposable for contact with a selected area of tissue within a patient's heart. It is desirable to construct the gripping members so that when open the exposed area available for ablating tissue is as large as is practical. The gripping members are able to apply gripping force to a contacted region of heart tissue for stabilizing the position of the catheter tip during an electrophysiological procedure. Ring electrode 28 is mounted on the catheter tip so that the outer surface of the electrode forms a smooth, continuous surface with the surface of the catheter shaft. An electrically conductive wire 36 provides electrical communication between the ring electrode and the proximal end of the catheter. A rubber seal 38 prevents the seepage of blood and other body fluids into the catheter through the distal end of the device.

Distal tube 22 defines a pair of non-coaxial lumens 40, 42. A deflection wire 44 extends into lumen 40 to a position near the distal end of the catheter where it is crimped onto a stainless steel hypotube 46 which is welded to a short length (e.g., 0.2 inches) of stainless steel ribbon 48 to form a "T" structure. The ribbon sits within an opening 50 in the wall of the catheter tip. The ribbon is larger than opening 50. The ribbon is bonded to the catheter tip by filling the opening with a biocompatible adhesive. Deflection wire 44 is coupled from the catheter tip to a piston 52 which is slidably disposed within a bore of a control handle 54. The catheter tip is deflected by gripping the control handle housing and moving the piston distally (shown by arrow 56) out of the piston chamber, which tenses the deflection wire and draws the distal end of the catheter proximally toward the handle. Because the deflection wire is attached to one side of the catheter tip, the tip preferentially bends radially in the direction of attachment (shown in shadow in FIG. 1).

The deflection wire is preferably surrounded by a TEFLON™ sheath that extends from a location near the proximal end of the piston chamber to a distal location that is spaced proximally of the distal end of the deflection wire by at least a distance equal to the maximum operating length of longitudinal movement of the piston relative to the housing (e.g., ½ to ¾ inch). The sheath provides lubricity for the movement of the deflection wire, and also serves to maintain the deflection wire in generally coaxial relation with the catheter body 14. The deflection wire is maintained in coaxial relation with the catheter body so that the length of the deflection wire and the on-axis length of the catheter body are substantially the same, whether the catheter body extends around a curve or not. In this arrangement, less energy is required for rotation of the catheter tip. This allows the tip to be more responsive to rotation of the handle and therefore more easily controlled.

As shown in FIG. 1, an electrode actuation wire 60 is coupled between the gripping members and an electrode actuation knob 62 at the proximal end of the catheter. The gripping members are opened when the actuation knob is moved in the distal direction (shown by arrow 64), and the gripping members are closed when the actuation knob is moved the opposite direction. The diameter and the constituent material of the actuation wire are selected so that the actuation wire has sufficient axial stiffness to support the axial load necessary to open the gripping members. In a presently preferred embodiment, the electrode actuation wire is formed from conductive material (e.g., nitinol) and serves to deliver rf ablation energy to the gripping members.

Figure 2:
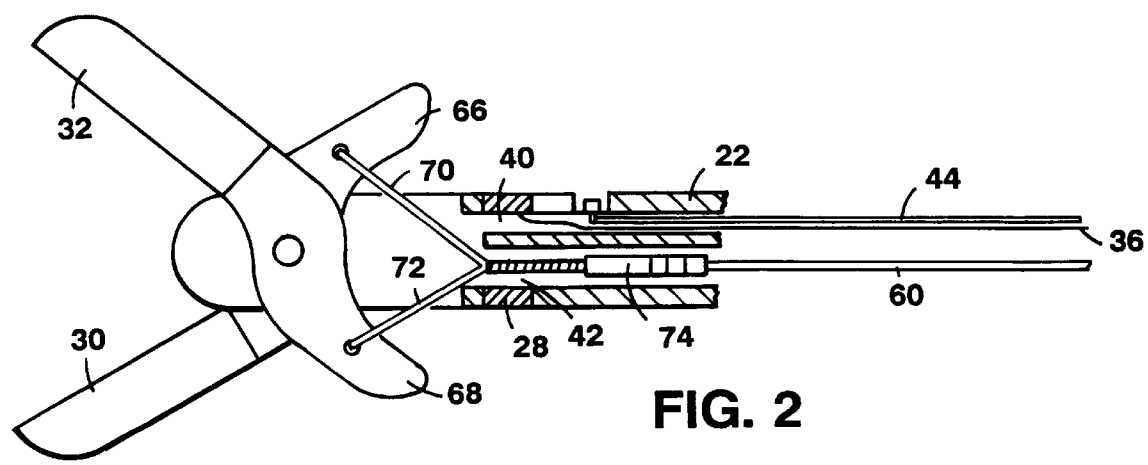
FIG. 2 is a diagrammatic cross-sectional side view of the distal tip of the catheter of FIG. 1.

As shown in FIG. 2, in a presently preferred embodiment, gripping members 30, 32 include respective proximal extensions 66, 68 onto which are looped respective wire strands 70, 72. The length of strand 70 is made longer than the length of strand 72, as shown. Strands 70, 72 are wound together and are coupled to actuation wire 60 by a crimp junction 74. Electrode actuation wire 60 and deflection wire 44 are respectively disposed in the non-coaxial lumens 40, 42 so that when the gripping members are closed, proximally-directed tension, applied by electrode actuation wire 60 to the catheter tip (urging displacement of the position of the catheter tip), is substantially counteracted by application of proximally-directed tension to deflection wire 44, as described below in connection with FIG. 3B. The radial position of the electrode actuation wire relative to the central axis of the catheter tip is adjusted to achieve the desired compensation effect (e.g., by changing the radial position and the size of lumen 42).

Referring to FIG. 3, control handle 54 includes a cylindrical housing 76 that has a cylindrical bore 78. Piston 52 has a distal end that is attached to the proximal end of the catheter shaft and a proximal end that is slidably disposed within the bore of housing 76. The proximal end of catheter body 14 fits within a bore defined by piston 52 and abuts against a lip region of the piston where the diameter of the piston bore is reduced. The catheter body is attached at the proximal end to the piston using, e.g., a cyanoacrylate adhesive.

Figure 3B:
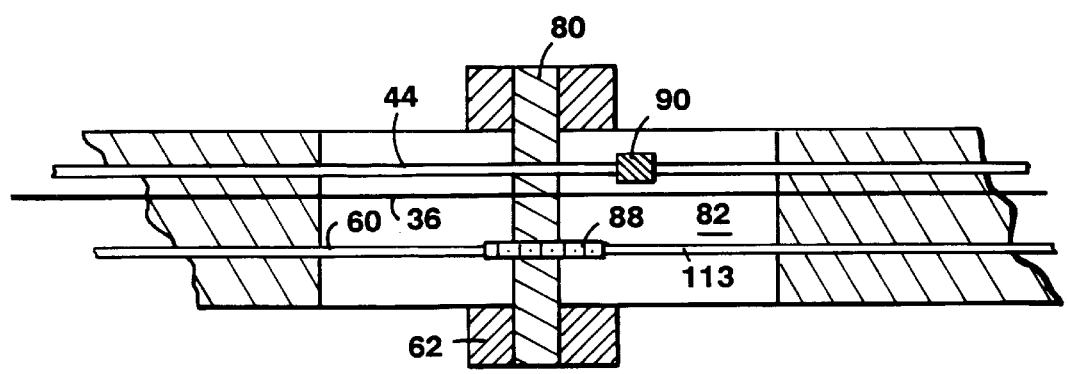
FIG. 3B is a cross sectional side view of the proximal end of the catheter shown in FIG. 3.

As shown in FIGS. 3A and 3B, electrode actuation knob 62 is mounted onto a slide bar 80 which freely slides within a slot 82 in piston 52. Slot 82 has a hole 84 through which deflection wire 44 passes and a hole 86 at which the proximal end of the electrode actuation wire is attached, e.g., by a solder crimp joint 88. A tracking device 90 (e.g., a stop) is attached to deflection wire 44 so that when the actuation knob is moved in the proximal direction to close the gripping members, the stopper is engaged by slide bar 80, which exerts tension on the deflection wire to compensate for the forces applied by the actuation wire that act to displace the position of the catheter tip. Thus, the tracking member tracks movement of the actuation wire and couples tension applied to the actuation wire to the deflection wire for counteracting force applied by the actuation wire to the distal portion of the catheter.

Referring back to FIG. 3, the handle housing is generally symmetrical about its longitudinal axis, allowing the handle to be freely rotated by an operator. The piston includes a circumferential O-ring notch 92 that carries an O-ring 94 to provide a watertight seal between the piston and the wall of the piston chamber. The piston includes a first slot 96 that extends along a portion of its length proximal of the o-ring notch. A set screw 98 extends from the wall of the housing into the slot. Slot 96 includes a keyway lock profile 100 (FIG. 3C). The set screw restricts the longitudinal movement of the piston by engaging the walls 102 of the keyway lock profile. To steer the catheter tip, the piston is pushed in and out of the slots 104, defined by the walls of lock profile 100, until a desired tip deflection is achieved. An annular thumbrest 108 is then twisted to lock the piston in place relative to the control handle housing.

A second slot 106 is disposed on the opposite side of the piston as the first slot. Within the second slot are two adjacent, short (e.g., ⅜ inch long) pieces of TEFLON™ tubing that provide a lubricous surface to facilitate axial movement of the piston with respect to the handle housing. The distal end of the piston extends beyond the distal end of the housing so that it may be manually controlled by a user. Annular thumbrest 108 is attached to the distal end of the piston to facilitate axial movement of the piston.

Deflection wire 44 extends through the axial bore of the piston, through hole 84 in slide bar 80 to the proximal end of handle housing 76, where it is attached by an anchor 110. The anchor extends into a transverse hole in the portion of the housing between the connector and the piston chambers.

The anchor is rotatable within the hole, but fits snugly so that it does not rotate freely. The anchor includes a transversely extending hole that may be rotated into alignment with the axis of the handle housing to receive the proximal end of the deflection wire. The anchor is rotated by means of a flat screw driver slot 112 to adjust the tension on the deflection wire.

Electrode actuation wire 60 and ring electrode lead wire 36 extend from the catheter body proximally through the axial bore of the piston to the proximal end of the control handle housing. An ablation electrode lead wire 113 is coupled to the electrode actuation wire at the actuation knob to provide electrical energy to the actuation wire (FIG. 3B). Preferably a TEFLON™ sheath surrounds and protects lead wires 36, 113 in the piston chamber. At the proximal end of the handle housing the lead wires and the surrounding sheath are bowed slightly to provide slack as the catheter is manipulated. The lead wires are connected to a rotary connector that includes a conventional cylindrical male plug 114 (e.g., a NEXUS198 plug) that extends proximally from the handle housing. The plug has a series of terminals along its length, each of which is connected to a separate lead wire within the connector chamber. These terminals operate independently of each other and allow separate electrical signals to be transmitted through the connector simultaneously.

A closely wound spring coil 116 is disposed within the lumen of the catheter shaft. The coil extends distally from the proximal end of catheter body 14 to near the distal end of the catheter body. The coil structure efficiently transmits torque from the proximal end of the catheter to the catheter tip because the direction of the applied torque substantially corresponds to the incompressible axis of the coiled wire. In a presently preferred embodiment, the proximal end of the coil is securely attached to the proximal end of the catheter body, but the distal end of the coil is unattached to the catheter body. This allows a certain amount of stretch in the portion of the coils on the outside portion of a bent region of the catheter body, thereby achieving a high flexibility while providing the efficient torque-transmitting capability of the coil. In other words, as the catheter body is bent e.g., through the aortic arch, the upper part of the coil opens up to maintain the flexibility, but the inner portion of the coil is tight in compression. In this position, the coil, together with the catheter body, are able to transmit torsional and tensile forces exerted on the proximal end of the catheter. Further details regarding the arrangement of the coil and the catheter shaft are provided in U.S. Ser. No. 08/138,863, filed Oct. 19, 1993, which is herein incorporated by reference.

In a presently preferred embodiment, the gripping members are made of stainless steel and are each about 4 mm long so that when the ablation electrode is fully open the gripping members extend over a length of about 8 mm. The ring electrode is made of platinum and is about 1.3 mm wide. The electrode actuation wire is made of nitinol and has a diameter of about 0.018–0.019 inch. The deflection wire is made of nitinol and has a diameter of about 0.01 inch. Typically a force of about 10–12 pounds is required to deflect the distal portion of the catheter by one hundred and eighty degrees. Preferably, the handle and piston are formed from acetal (e.g., DELRIN™). The length of the catheter shaft is about 48 inches (120 cm), while the length of the catheter tip is typically between 1½ and 3 inches (3.8–7.6 cm). The outer diameter of the catheter body is typically about 7 French (0.23 cm), and the outer diameter of the catheter tip is typically about 6 French (0.2 cm). Of course, the choice of the catheter dimensions will depend upon the anatomy of the patient and the type of procedure to be performed. The braided shaft is formed from counter-wound double stainless steel wires with a pick count (i.e., the number of times that wires cross a unit of tube length) of about thirty-two to thirty-four times per inch that are braided over a polyurethane tube which is over-extruded with a polyurethane coating that bonds through the braid to the inner tubing to form a unitary structure with a hardness of about D70. The distal portion of the catheter shaft is formed from a polyurethane extrusion and preferably has a hardness of about D60. The spring coil 72 has an inside diameter of about 0.038 inch (0.10 cm) and an outside diameter of about 0.058 inch (0.15 cm), and fits closely within the inside diameter of the shaft 30, which is about 0.059–0.062 inch (0.15–0.16 cm). The coil is made from e.g., #302 stainless steel wire that has a circular cross-section (although a wire with a rectangular cross-section may be used). The coil may be fabricated from other spring-like materials, such as nitinol.

During fabrication of catheter 10, catheter body 14 slides over a tip assembly that includes catheter tip 18 with the ring and ablation electrodes, the deflection and electrode actuation wires, and the ring electrode lead wire. All of the wires are pulled through the catheter body. The spring coil slips over the proximal end of the deflection wire and over the electrical lead wires and into the catheter body. The proximal end of the catheter body is then attached to the distal end of the piston portion of the control handle.

OPERATION

Referring to FIG. 4, in an electrophysiology procedure, deflectable ablation catheter 10 is introduced through an introducer sheath into the right femoral artery of a patient 120 by use of the Seldinger technique (alternatively, the catheter may be introduced through the left femoral artery, or the right or left femoral veins depending upon the region of the heart to be accessed). An operator advances the catheter under fluoroscopic guidance through the patient's vasculature by simultaneously deflecting the distal tip of the catheter and applying torque to the proximal end of the catheter. The catheter is advanced through the inferior vena cava until the catheter tip 18 is positioned in a chamber of the patient's heart 122 (e.g., in the right atrium 124). The catheter enters the right atrium in an undeflected state. The operator maneuvers steerable tip 18 around the anatomical structure of the heart to position the ablation electrode into the region of the heart that is to be mapped or ablated (e.g., the right ventricle 126). Thus, the deflectability of the catheter permits the operator to accurately position the electrodes against the desired portion of the heart wall.

Referring to FIG. 4A, with gripping members 30, 32 in closed position, the ablation electrode and ring electrode 28 are used to locate the region of the heart wall that is to be ablated. Differential electrical signals from the heart wall and the blood volume within the right ventricle are detected between the ring electrode and the ablation electrode (or between the ring electrode and one or more additional ring electrodes, if present). These signals are delivered through electrical wire 36 and electrode actuation wire 60 to a processor and to a display device for analysis.

Referring to FIG. 4B, when the location of the abnormal region of heart tissue is determined, the gripping members are opened by moving the electrode actuation knob distally (as indicated by arrow 64 in FIG. 1). With the gripping members fully open, the catheter tip is deflected by pushing distally on thumbrest 108 (indicated by arrow 56 in FIG. 1), which presses the gripping members against the myocardial tissue, increasing the normal force 128 applied by the ablation surfaces of the gripping members. The deflection of the catheter tip is locked in place by twisting the piston relative to the handle housing. The operator then moves the actuation knob in the proximal direction to partially close the gripping members, thereby actively fixing (gripping) the catheter tip onto the tissue to be ablated. Rf energy is delivered through the electrode actuation wire to the gripping members until the desired amount of myocardial tissue is ablated (e.g., for a period of about 30 seconds to 1 minute). The combination of the fixation feature and the large surface area of the gripping members exposed for contact with heart tissue enables deep, large area ablations to be achieved with a high degree of control.

Other embodiments are within the scope of the claims.

Referring to FIG. 5, in an alternative embodiment, instead of flat surfaces, gripping members 30, 32 include respective arrays of teeth 130, 132 that mate together when the gripping members are closed. Teeth 130, 132 provide additional gripping force to hold the position of the ablation surfaces of the gripping members against the region of the heart to be ablated.

Alternatively, as shown in FIGS. 6 and 6A, an axially oriented needle 140 is mounted on the distal end of the catheter. Needle 140 is constructed to penetrate the heart wall to a selected depth (e.g., 1–3 mm) beyond the ablation surfaces of the gripping members. To allow the gripping members to close, a needle-shaped recess 142 is provided in the ablation surfaces of the gripping members. The needle preferably has an outer diameter of about 0.015 inch. To increase the fixing force of the ablation electrode against the heart wall, sufficient sideways (parallel to the local surface of the heart wall) pressure may be applied to the catheter tip to increase the resistance to removal of the needle. Needle 140 may be electrically insulating or electrically conducting; if electrically conducting, the needle will increase the depth of ablation achievable by the ablation electrode.

We note the following co-pending applications, which are all herein incorporated by reference: Ser. No. 08/138,863, filed Oct. 19, 1993, U.S. Ser. No. 08/038,903, filed Mar. 29, 1993, now U.S. Pat. No. 5,403,311, and U.S. Ser. No. 08/086,543, filed Jul. 1, 1993.

Still other embodiments are within the scope of the claims.

What is claimed is:

1. A deflectable catheter for ablating tissue in the heart of a patient comprising an axially elongated catheter shaft having proximal and distal portions respectively terminating at proximal and distal ends, the catheter shaft being sized and constructed to be advanced through the vasculature of a patient into the patient's heart, a deflection wire coupled to the distal portion of the catheter shaft and extending within the catheter shaft to the proximal end thereof, an ablation electrode coupled to the distal end of the catheter shaft and having first and second opposed electrically conductive surfaces exposable for contact with a selected area of tissue within the patient's heart, and an elongated electrode actuator extending through the catheter shaft and attached to the ablation electrode to effect movement of the first and second surfaces of the electrode with respect to each other to apply gripping force to the contacted area of heart tissue for stabilizing the position of the electrically conductive surfaces of the ablation electrode relative to the selected area of heart tissue.

2. The deflectable catheter of claim 1 wherein the ablation electrode is adjustable from a closed position in which the ablation electrode has an outer surface exposed for contact with the vasculature of the patient during advancement of the catheter therethrough to an open position in which the first and second electrically conductive surfaces are exposable for contact with tissue over an area larger than an axially transverse area circumscribed by the outer surface of the ablation electrode in the closed position.

3. The deflectable catheter of claim 1 wherein said electrode actuator is constructed and arranged to enable selective exposure of conductive surface of the ablation electrode to the selected area of heart tissue.

4. The deflectable catheter of claim 1 wherein the ablation electrode comprises two opposed gripping members that are movable relative to each other between an open position and a closed position, and said electrode actuator is coupled to the two gripping members and extending proximally therefrom to the proximal end of the catheter shaft for moving the gripping members.

5. The deflectable catheter of claim 4 further comprising a tracking member coupled to the deflection wire and constructed and arranged to track movement of the electrode actuator and to couple tension on the electrode actuator to the deflection wire to counteract force applied by the electrode actuator to the distal portion of the catheter shaft during movement of the gripping members.

6. The deflectable catheter of claim 4 wherein the opposed gripping members together form a generally dome-shaped outer surface.

7. The deflectable catheter of claim 4 wherein the opposed gripping members are formed of solid electrically conductive members that have opposed flat surfaces exposable for contact with the selected area of tissue, the opposed gripping members being pivotally hinged together about a pivot bearing.

8. The deflectable catheter of claim 1 wherein conductive surface of the ablation electrode that is exposable for contact with the selected area of heart tissue is characterized by mechanical rigidity and flatness over an extended area having transverse dimension of comparable size.

9. The deflectable catheter of claim 1 wherein conductive surface of the ablation electrode exposable for contact with the selected area of heart tissue comprises a plurality of teeth for engaging heart tissue.

10. The deflectable catheter of claim 1 further comprising a needle coupled to the distal end of the catheter shaft and constructed and arranged to penetrate heart tissue to a selected depth.

11. A deflectable catheter for ablating tissue in the heart of a patient comprising an axially elongated catheter shaft having proximal and distal portions respectively terminating at proximal and distal ends, the catheter shaft being sized and constructed to be advanced through the vasculature of a patient into the patient's heart, a deflection wire coupled to the distal portion of the catheter shaft and extending within the catheter shaft to the proximal end thereof, and an ablation electrode coupled to the distal end of the catheter shaft, the ablation electrode being adjustable from a closed position in which the ablation electrode has an outer surface exposed for contact with the vasculature of the patient during advancement of the catheter therethrough to an open position in which the ablation electrode is exposable for contact with a selected area of tissue within the patient's heart over an area larger than an axially transverse area circumscribed by the outer surface of the ablation electrode in the closed position.

12. A method for the therapeutic treatment of the heart of a patient by ablation of a selected area of heart tissue comprising the steps of:

positioning an axially elongated catheter within the heart of a patient, the catheter having a distal ablation electrode with an exposable electrically conductive surface;

exposing the electrically conductive surface of the ablation electrode to a selected area of heart tissue;

gripping the selected area of heart tissue with the exposed electrically conductive surface of the ablation electrode to stabilize the position of the electrically conductive surface relative to the selected area of heart tissue; and ablating the selected area of heart tissue by supplying to the electrically conductive surface of the ablation electrode energy sufficient to achieve tissue ablation.

13. The method of claim 12 further comprising the step of deflecting a distal portion of the catheter to increase pressure applied by the exposed conductive surface of the ablation electrode against the selected area of heart tissue.

14. The method of claim 12 further comprising the step of selecting the area of heart tissue to be ablated by measuring the electrical potentials within the patient's heart using the catheter positioned within the heart.

15. A method for the therapeutic treatment of the heart of a patient by ablation of a selected area of heart tissue comprising the steps of:

providing an axially elongated catheter having a distal ablation electrode adjustable from a closed, low-profile position to an open position in which an electrically conductive rigid surface of the ablation electrode is exposable for contact with heart tissue over an area larger than an axially transverse area circumscribed by the rigid surface of the ablation electrode in the closed position;

advancing the catheter through the vasculature of a patient and into the patient's heart with the ablation electrode in the closed position;

adjusting the ablation electrode into the open position to expose the electrically conductive rigid surface of the ablation electrode for contact with a selected area of heart tissue;

contacting the selected area of heart tissue with the electrically conductive rigid surface of the ablation electrode; and ablating the selected area of heart tissue by supplying to the electrically conductive surface of the ablation electrode energy sufficient to achieve tissue ablation.

16. The method of claim 15 further comprising the step of deflecting a distal portion of the catheter to increase pressure applied by the exposed conductive surface of the ablation electrode against the selected area of heart tissue.

17. The method of claim 15 further comprising the step of selecting the area of heart tissue to be ablated by measuring the electrical potentials within the patient's heart using the catheter positioned within the heart.

* * * * *

UNITED STATES PATENT AND TRADEMARK OFFICE
CERTIFICATE OF CORRECTION

PATENT NO.    : 6,083,222
DATED         : July 4, 2000
INVENTOR(S)   : George J. Klein, Josef V. Koblish and Thomas T. Coen Page 1 of 1

It is certified that error appears in the above-identified patent and that said Letters Patent is hereby corrected as shown below:

<u>Column 7,</u>
Line 20, please delete "NEXUS198" and insert -- NEXUS™ --

Signed and Sealed this

Twenty-third Day of July, 2002

Attest:

Attesting Officer

JAMES E. ROGAN
Director of the United States Patent and Trademark Office